United States Patent
Sakimoto et al.

(10) Patent No.: US 10,950,012 B2
(45) Date of Patent: Mar. 16, 2021

(54) RADIATION IMAGE GENERATION METHOD AND IMAGE PROCESSING DEVICE

(71) Applicant: SHIMADZU CORPORATION, Kyoto (JP)

(72) Inventors: Tomonori Sakimoto, Kyoto (JP); Kazuyoshi Nishino, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/541,962

(22) PCT Filed: Jan. 9, 2015

(86) PCT No.: PCT/JP2015/050549
§ 371 (c)(1),
(2) Date: Jul. 6, 2017

(87) PCT Pub. No.: WO2016/111016
PCT Pub. Date: Jul. 14, 2016

(65) Prior Publication Data
US 2018/0025513 A1 Jan. 25, 2018

(51) Int. Cl.
*G06K 9/00* (2006.01)
*G06T 11/00* (2006.01)
(Continued)

(52) U.S. Cl.
CPC .............. *G06T 11/008* (2013.01); *A61B 6/03* (2013.01); *A61B 6/04* (2013.01); *A61B 6/4208* (2013.01);
(Continued)

(58) Field of Classification Search
CPC .... G06T 11/006; G06T 11/008; G06T 11/003; G06T 11/005
See application file for complete search history.

(56) References Cited

U.S. PATENT DOCUMENTS 6,137,856 A * 10/2000 Lin ................. G06T 11/006
378/4
6,272,200 B1 * 8/2001 Pan ................. G06T 11/005
378/15
(Continued)

FOREIGN PATENT DOCUMENTS

JP 2002-150266 5/2002
JP 2003-153893 5/2003
(Continued)

OTHER PUBLICATIONS

PCT/JP2015/050549, ISR and Written Opinion, dated Mar. 31, 2015, 7 pages—Japanese; 5 pages—English.

*Primary Examiner* — Avinash Yentrapati
(74) *Attorney, Agent, or Firm* — Andrew F. Young, Esq.; Nolte Lackenbach Siegel (57) ABSTRACT

An image processing element 9 of the present invention includes a weighting factor setting element 9a that sets up a weighting factors $w_{nn}$, $w_{bi}$ of the weight addition combing a nearest neighbor interpolation and a bilinear interpolation based on an absolute value $|I_{bi} - I_{nn}|$ of the difference between the pixel value $I_{nn}$ acquired by the nearest neighbor interpolation and the pixel value $I_{bi}$ acquired by the bilinear interpolation; and a weight addition element 9b that implement a weighting addition based on the set-up weighting factors $w_{nn}$, $w_{bi}$. A reconstructed image can be acquired by arranging the backprojection pixel value $I_{new}$ every pixel following the weighting. A reconstructed image can be obtained in which any noise and artifacts are reduced by setting the weighting factor of the image processing algorithm causing a negative effect on the region of some pixel values to be minimal and setting the weighting factor of the (other) image processing algorithm causing a positive-effect
(Continued)

on the same pixel value region to be maximum based on the absolute value $|I_{bt}-I_{nn}|$ of the difference.

3 Claims, 8 Drawing Sheets

(51) Int. Cl.
    *A61B 6/03*           (2006.01)
    *A61B 6/00*           (2006.01)
    *A61B 6/04*           (2006.01)
    *G06T 3/40*           (2006.01)
    *A61B 6/02*           (2006.01)

(52) U.S. Cl.
    CPC ............ *A61B 6/461* (2013.01); *A61B 6/5205* (2013.01); *A61B 6/5258* (2013.01); *A61B 6/54* (2013.01); *G06T 3/4007* (2013.01); *G06T 11/006* (2013.01); *A61B 6/025* (2013.01); *A61B 6/487* (2013.01); *G06T 2207/10116* (2013.01)

(56) References Cited

U.S. PATENT DOCUMENTS

| | | | | |
|---|---|---|---|---|
| 6,285,732 | B1* | 9/2001 | Hsieh | G06T 11/005 378/4 |
| 6,339,632 | B1* | 1/2002 | Besson | G06T 11/005 378/15 |
| 6,587,537 | B1* | 7/2003 | Hsieh | G06T 11/005 378/15 |
| 6,980,681 | B1* | 12/2005 | Hsieh | A61B 6/032 250/363.02 |
| 2003/0194048 | A1* | 10/2003 | De Man | G06T 11/006 378/4 |
| 2003/0223533 | A1* | 12/2003 | Hsieh | G06T 11/005 378/19 |
| 2004/0136608 | A1* | 7/2004 | Rosenfeld | G06T 3/4007 382/276 |
| 2004/0156469 | A1* | 8/2004 | Nishide | G06T 11/006 378/19 |
| 2010/0119034 | A1* | 5/2010 | Hein | A61B 6/032 378/19 |

FOREIGN PATENT DOCUMENTS

| | | |
|---|---|---|
| JP | 2004-313391 | 11/2004 |
| JP | 2005-522304 | 7/2005 |
| JP | 2010/115475 | 5/2010 |

* cited by examiner

RADIATION IMAGE GENERATION METHOD AND IMAGE PROCESSING DEVICE

CROSS REFERENCE TO RELATED APPLICATIONS

This application relates to, and claims priority from Ser. No.: PCT/JP2015/050549 filed Jan. 9, 2015, the entire contents of which are incorporated herein by reference.

FIGURE SELECTED OR PUBLICATION

FIG. 2
[This incorporates the required priority cross-reference and publication reference.]

TECHNICAL FIELD

The present invention relates to a radiograph generation method that generates a radiograph and an image processing apparatus that performs an image processing to generate the radiograph.

BACKGROUND

Hereinafter, the inventor sets forth e.g., a reconstructed image as a radiograph. A backprojection is applied to generation methods of a number of radiation tomographic images (image reconstruction). One of general backprojection methods is a pixel driven method. According to the pixel driven method, a ray is lined from an X-ray source to an X-ray detector passing the center of the reconstructed pixels. The pixel value assigned to the reconstructed pixels is determined by the pixel value on the X-ray detector near the location at which the X-ray detector surface and the ray cross. Typically, the linear interpolation determines the pixel value assigned to the reconstructed pixels (e.g., Patent Document 1, 2). An interpolation method applied to the reconstruction includes a bilinear interpolation (method) and a nearest neighbor interpolation (method), which are listed in Patent Document 2; JP 4,293,307 (JP2005/522304).

RELATED PRIOR ART DOCUMENTS

Patent Document

Patent Document 1
JP 2010-115475 A1
Patent Document 2
Patent Document 1: JP Patent 4293307 B1

ASPECTS AND SUMMARY OF THE PRESENT INVENTION

Objects to be Solved

Figure 5:
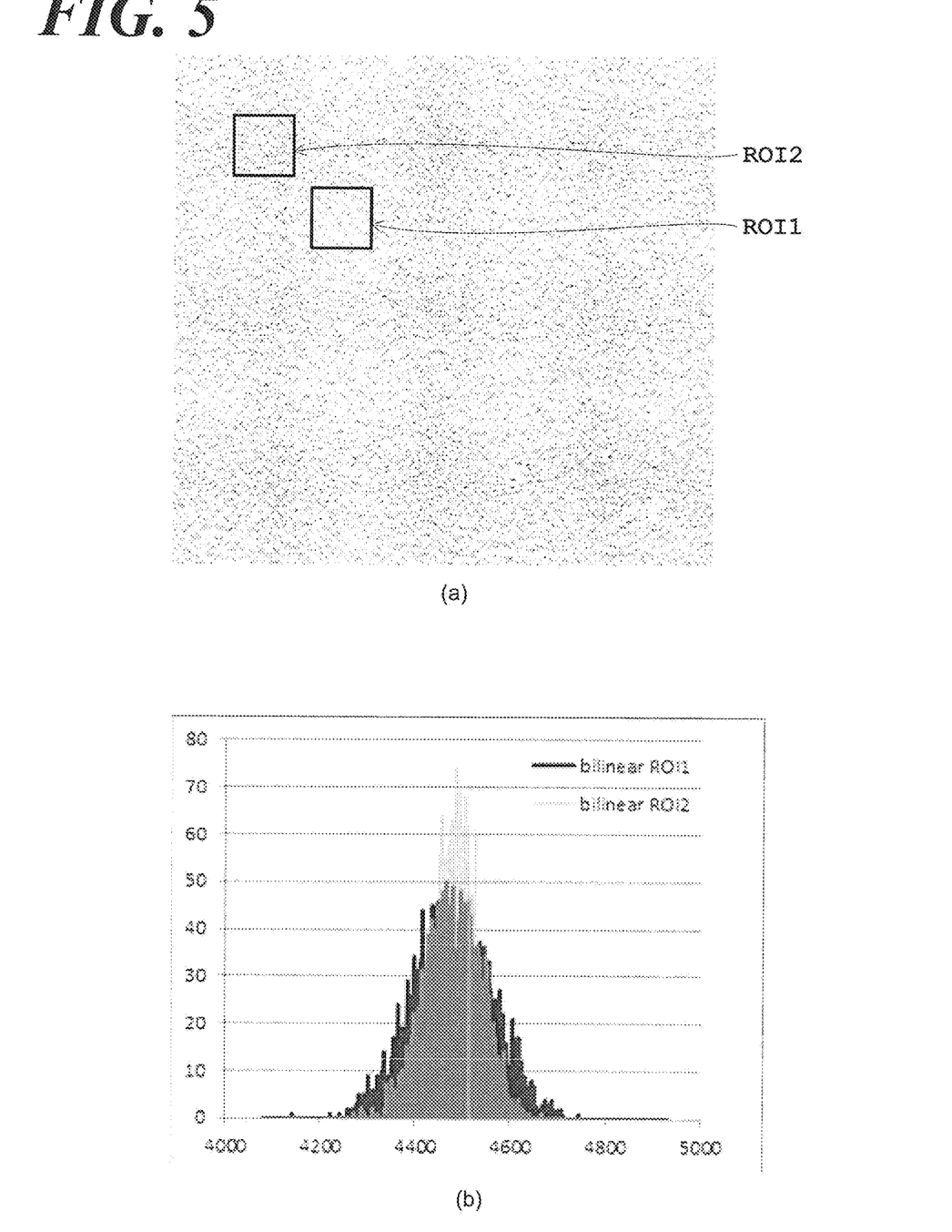
FIG. 5(a) is a normal distribution noise image reconstructed by the filtered backprojection method, in which the bilinear interpolation is the interpolation method.
FIG. 5(b) is a pixel value distribution thereof.

It is problematic, however, that non-uniformity of S/N (signal-to-noise) takes place due to the interpolation (method) depending on the crossing location between the X-ray detector and the ray upon the backprojection. FIG. 5(a) is a normal distribution noise image reconstructed by the filtered backprojection method, in which the bilinear interpolation is the interpolation method, and FIG. 5(b) is a pixel value distribution thereof. In addition, for convenience of figuring, black and white are inversed in FIG. 5(a), and practically, it is noted that noises appear as white spots on the black image in whole. Referring to FIG. 5(b), it is confirmed that the variance of pixel values is different between locations (RO11, RO12 in FIG. 5(b)).

Figure 6:
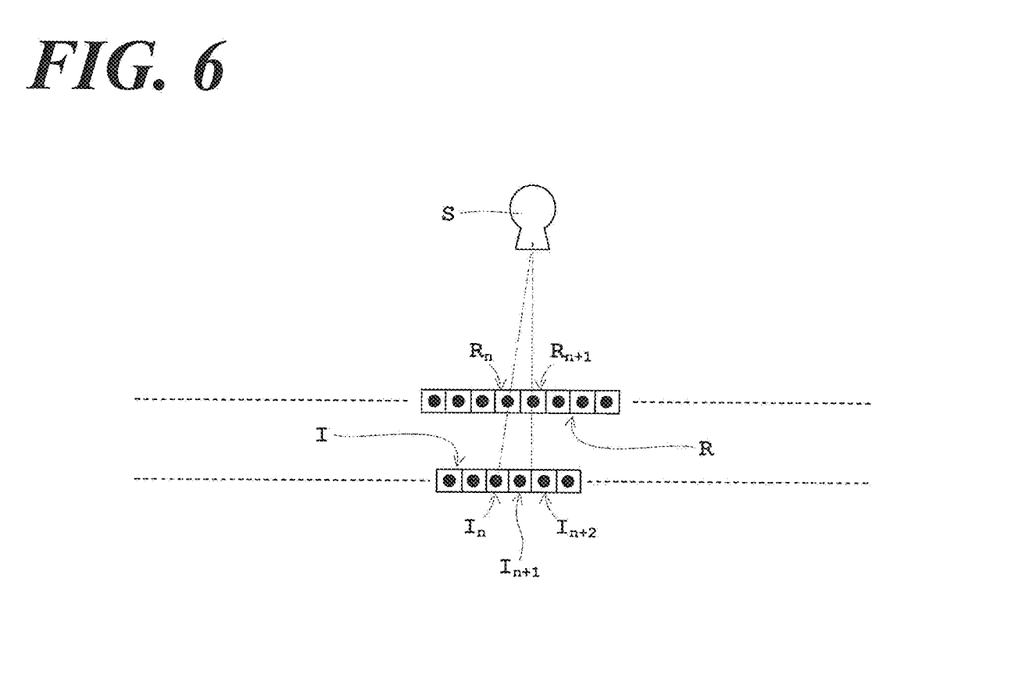
FIG. 6 is a schematic diagram illustrating an arrangement of a light source, a reconstructed image and a detector when a linear interpolation method is applied to the interpolation method relative to reconstruction.

Pixel values of only X-ray detector $I_n$ are reflected in the reconstructed image $R_n$ in the case referring to FIG. 6 (in which the sign S is an X-ray tube as a radiation source, the sign R is a reconstructed image, and the sign I is a detector) when a linear interpolation, such as bilinear interpolation, is applied to the interpolation method relative to the reconstruction. On the other hand, an average of pixel values of X-raydetector $I_{n+1}$ and $I_{n+2}$ is reflected in the reconstructed image $R_{n+1}$. Consequently, non-conformity of S/N appears in such reconstructed image.

A more precise interpolation algorithm is used to reduce such non-conformity of S/N. For example, while the interpolation using the Lanczos interpolation may reduce such non-conformity, but an increase of the calculation cost, an increase of the load, and a long-time calculation takes place as another problem. Another alternative method to reduce such non-conformity of S/N is the above nearest neighbor interpolation to determine the pixel values. Such a method is convenient and fess costly, and requires a less load and a short-time calculation. Another problem, however, is an occurrence of unevenness in the proximity of the pixel value edge of the reconstructed image. For example, when an extremely different pixel value is extending in a linear fashion relative to the surrounding pixel value thereof; such line is the pixel value edge, but an unevenness takes place in such line per se.

The problems discussed above take place not only relative to the backprojection relative to the reconstruction, but also even relative to the image processing including such as rotation, expansion and reduction, so it is desirable that an easy and convenient image processing algorithm reduces noises or artifacts (e.g., uneven artifacts and grid artifacts due to non-conformity of S/N).

Considering such circumstances, the object of the present invention is to provide a radiograph generation method and an image processing apparatus, capable of reducing noises and artifacts.

Means for Solving the Problem

The present invention comprises the following structure to solve such problem.

Specifically, a radiograph generation method according to the present invention is the radiograph generation method, which generates a radiograph, comprises;

a step of setting a weighting factor, which sets a weighting factor (coefficient) of a weight addition combining each image processing algorithm based on results of the respective pixel values acquired by a plurality of discrete image processing algorithms;

a step of implementing the weight addition based on the set-up weighting factor; wherein the radiograph is acquired by the weight addition.

The radiograph generation method according to the present invention performs the weight addition combining discrete image processing algorithms to combine a plurality of discrete image processing algorithms. For such purpose, the radiograph generation method sets weight addition weighting factor based on the results of the respective pixel values acquired by the respective image processing algorithms. The radiograph generation method acquires a radiograph, in which noise and artifacts are reduced by setting the weighting factor of the image processing algorithm causing a negative effect on the region of some pixel values to be minimal and setting the weighting factor of the (other) image processing algorithm causing a positive effect on the same pixel value region to be maximum based on the results of the pixel values acquired by the respective image processing algorithms.

One example of radiographs is a reconstructed image. For such a purpose, the radiograph generation method sets a weighting factor based on the results of the respective pixel values acquired by the respective image processing algorithms.

The weighting factor corresponding to every image processing algorithm can be set up independently from each other (the former) or the respective factors can be set up cooperatively as below (the latter). Specifically, in the latter case, the weighting factor corresponding to every image processing algorithm is a non-negative value less than 1 and n is an integer bigger than 2; and given each weighting factor is $w_1, w_2, \ldots, w_n$, each weighting factor is set as satisfying $w_1+w_2+\ldots+w_n=1$. In such way, discrete weighting factors satisfying $w_1+w_2+\ldots+w_n=1$ is set up, so that the discrete weighting factors can be set up cooperatively. Accordingly, when it is desirable that the effect of a certain image processing algorithm is strong, the weighting factor relative to such image processing algorithm is set to be large, so that the weighting factor relative to the rest of image processing algorithms can be set to be small. Reversely, when it is desirable that the effect of a certain image processing algorithm is weak, the weighting factor relative to such image processing algorithm is set to be small, so that the weighting factor relative to the rest of image processing algorithms can be set to be large.

Specific image processing algorithm is not particularly limited. A spline interpolation method other than the nearest neighbor interpolation, the bilinear interpolation, and Lanczos interpolation, as discussed above, can be applied. Considering that even simple interpolation algorithms can, however, reduce noises and artifacts, an easy and convenient interpolation algorithm, such as the nearest neighbor interpolation, the bilinear interpolation or the spline interpolation method, are more advantageous than such precious interpolation algorithms such as the Lanczos interpolation. Reducing not only the calculation cost, the loading, the calculation-time, but also noises and artifacts can be achieved by applying such easy and convenient algorithm.

Accordingly, the image processing algorithm is the nearest neighbor interpolation and the bilinear interpolation; in which it is preferable that the image processing algorithm sets up the weighting factor based on the result of the respective pixel values obtained by the nearest neighbor interpolation and the bilinear interpolation relative to the weighting factor set-up step, and implements the weight addition in regard to the nearest neighbor interpolation and the bilinear interpolation relative to the weight addition step. The bilinear interpolation sets up the weighting factor in the region (region having the edge with high-intensity difference) so as to be large, at which the negative effect due to the nearest neighbor interpolation is strong, so that the bilinear interpolation can reduce the uneven artifact. Reversely, the nearest neighbor interpolation sets up the weighting factor in the region (region having the non-conformity of S/N) so as to be large, at which the negative effect due to the bilinear interpolation is strong, so that the nearest neighbor interpolation can reduce the grid artifact due to the non-conformity of S/N. In such way, the nearest neighbor interpolation and the bilinear interpolation can reduce not only the calculation cost, the loading, the calculation-time, but also the uneven artifact and the grid artifact due to the non-conformity of S/N, despite such easy and convenient interpolation algorithm.

When the image processing algorithms are the nearest neighbor interpolation and the bilinear interpolation, such image processing algorithm is useful for the following invention. Specifically, it is useful when the radiograph is the reconstructed image, X-ray is applied, and the weighting factor is set up based on the results of the backprojection pixel values acquired by the nearest neighbor interpolation and the backprojection pixel values acquired by the bilinear interpolation. In such way, when the radiation is an X-ray, the above uneven artifact and the grid artifact due to non-conformity of S/N easily take place; but when the weighting factor is set up based on the results of the backprojection pixel values acquired by the nearest neighbor interpolation and the backprojection pixel values acquired by the bilinear interpolation, the uneven artifact and the grid artifact due to non-conformity of S/N can be reduced.

When the image processing algorithms are the nearest neighbor interpolation and the bilinear interpolation, the radiograph is the reconstructed image and the radiation is the X-ray; the following setting is preferable. Specifically, it is preferable that based on the absolute value of the difference between the pixel values acquired by the nearest neighbor interpolation and the pixel values acquired by the bilinear interpolation, the weighting factor for the bilinear interpolation is being set to be large in accordance with increasing of the absolute value of the difference between the pixel values acquired by the nearest neighbor interpolation and the pixel values acquired by the bilinear interpolation; and the weighting factor for the nearest neighbor interpolation is being set to be large in accordance with decreasing of the absolute value of such difference. The region at which the absolute value of the difference set forth above is deemed as the edge with high-intensity difference, and then the weighting factor for the bilinear interpolation is set to be large (i.e., strengthen the weight), so the unevenness at such edge region can be reduced. Reversely, the nearest neighbor interpolation sets up the weighting factor to be large in the region at which the absolute value of the difference set forth above is small (i.e., strengthen the weight), so that the grid artifact due to the non-conformity of S/N can be reduced.

Further specifically, it is preferable that the following respective weighting factors are set up cooperatively. Specifically, when the weighting factor corresponding to the nearest neighbor interpolation is a non-negative value less than 1, the weighting factor for the nearest neighbor interpolation is $w_{nn}$ and the weighting factor for the bilinear interpolation is $w_{bi}$, it is preferable that each weighting factor is set up so as to satisfy $w_{nn}+w_{bi}=1$. The region at which the absolute value of the difference set forth above is deemed as the edge with high-intensity difference, and then the weighting factor $w_{nn}$ for the nearest neighbor interpolation is set up to be small to reduce unevenness at such edge region, so that the weighting factors $w_{bi}$ for the bilinear interpolation can be large (i.e., strengthen the weight). Consequently, the unevenness in the edge region decreases. Reversely, relative to the region at which the absolute value of the difference set forth above is small, the weighting factors $w_{bi}$ for the bilinear interpolation is set up so as to be small, the rest of the weighting factor $w_{nn}$ for the nearest neighbor interpolation can be large (i.e., strengthen the weight). Consequently, the grid artifact due to the non-conformity of S/N decreases.

In addition, an image processing apparatus, according to the present invention is the image processing apparatus that performs an image processing to generate a radiograph, comprises:

a weighting factor setting means that sets up a weight addition weight factor combining each image processing algorithm based on the results of the respective pixel valued acquired by a plurality of discrete image processing algorithms; and a weight addition means that performs such weight addition based on the set-up weighting factor, wherein the radiograph is acquired by such weight addition.

According to the image processing apparatus of the present invention, the radiograph generation method acquires a radiograph, in which noises and artifacts are reduced by setting the weighting factor of the image processing algorithm causing a negative effect on the region of some pixel values to be minimal and setting the weighting factor of the (other) image processing algorithm causing a good-effect on the same pixel value region to be maximum based on the results of the respective pixel values acquired by the respective image processing algorithms.

Effect of the Invention

According to the radiograph generation method and the image processing apparatus of the present invention, the radiograph generation method acquires a radiograph, in which noises and artifacts are reduced by setting the weighting factor of the image processing algorithm causing a negative effect on the region of some pixel values to be minimal and setting the weighting factor of the (other) image processing algorithm causing a positive effect on the same pixel value region to be maximum based on the results of the respective pixel values acquired by the respective image processing algorithms.

BRIEF DESCRIPTION OF THE DRAWINGS

FIG. 7(a) is the image acquired using the nearest neighbor interpolation. FIG. 7(b) is the image acquired using the bilinear interpolation. FIG. 7(c) is the image acquired using the method according to the present invention.

FIG. 8(a) is the image acquired using the nearest neighbor interpolation. FIG. 8(b) is the image acquired using the bilinear interpolation. FIG. 8(c) is the image acquired using the method according to the present invention.

EMBODIMENTS

Figure 1:
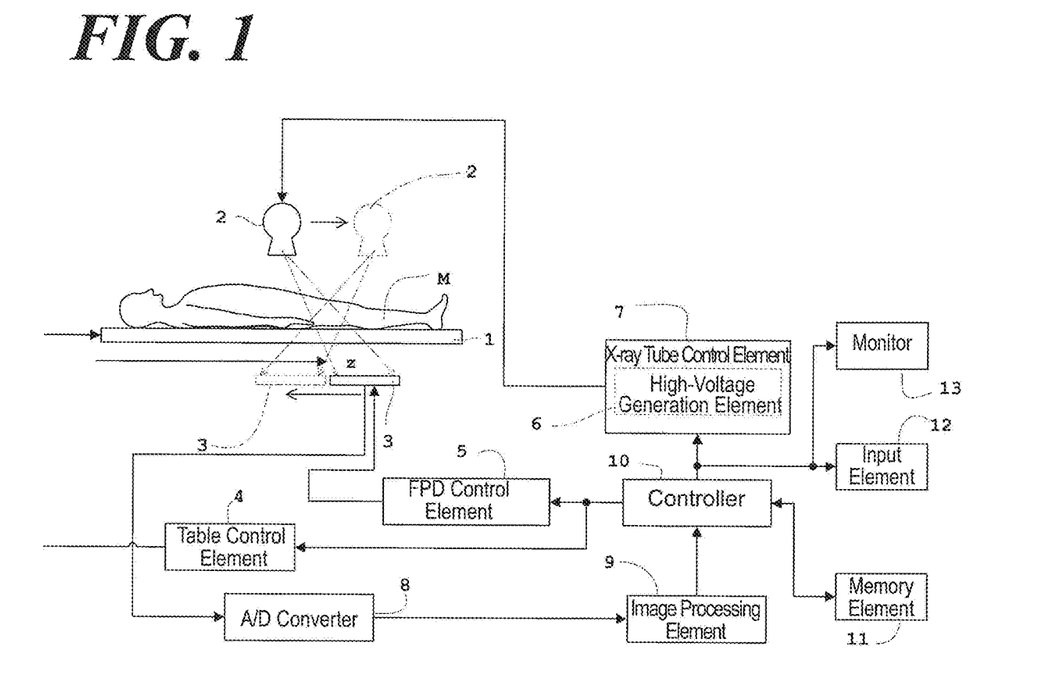
FIG. 1 is a block diagram illustrating a tomographic imaging apparatus according to an aspect of the Embodiment 1.
Figure 2:
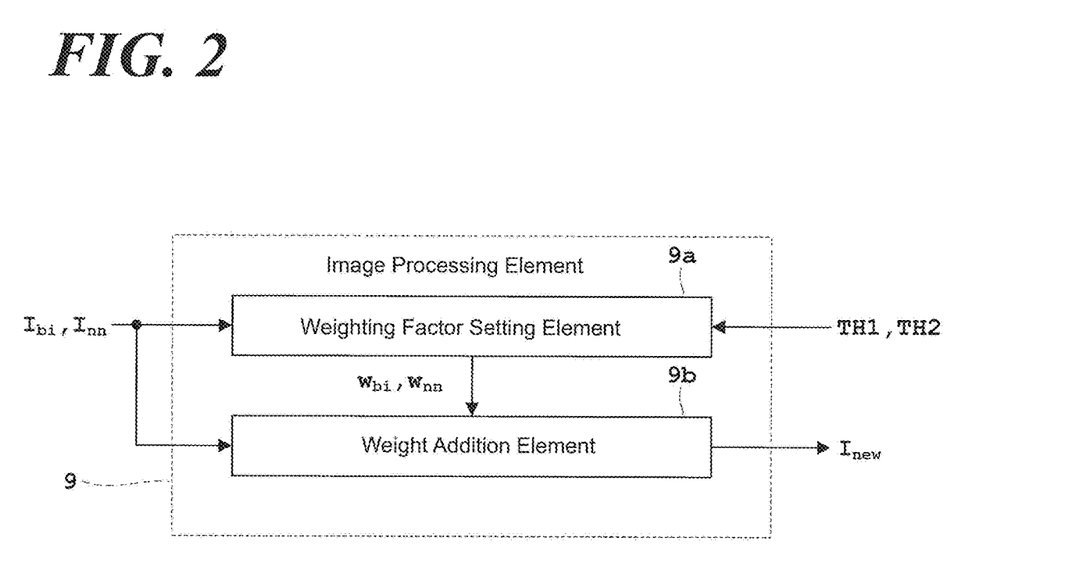
FIG. 2 is a block diagram illustrating an image processing element of the tomographic imaging apparatus according to the aspect of Embodiment.

Referring to Figures, the inventor sets forth the Embodiment of the present invention. FIG. 1 is a block diagram illustrating a tomographic imaging apparatus according to the aspect of Embodiment and FIG. 2 is a block diagram illustrating an image processing element of the tomographic imaging apparatus according to the aspect of Embodiment. According to the aspect of the Embodiment of the present invention, the inventor sets forth the present invention based on e.g., a reconstructed image as a radiograph, and an X-ray as the radiation. In the present Embodiment 3, the inventor sets forth e.g., a human as a subject.

Referring to FIG. 1, the tomographic imaging apparatus comprises; a table 1 on which a subject M is laid, an X-ray tube 2 to irradiate X-ray to the subject M and a flat panel type X-ray detector 3 (FPD 3) to detect the X-ray transmitted through the subject.

The tomographic imaging apparatus further comprises; a table control element 4 that controls lifting and horizontal movement of table 1; a FPD control element 5 that controls the scanning of FPD 3; an X-ray tube control element 7 having a high-voltage generation element 6 that generates a tube voltage of the X-ray tube 2 and a tube electric current; an image processing element 9 that implements a variety of processings based on an X-ray signal output from the A/D converter 8; a controller 10 that controls the respective units; a memory element 11 that stores such as a processed image; an input element 12 that allows an operator to conduct an input-setting; and a monitor 13 that displays such as the processed image. The image processing device 9 corresponds to the image processing apparatus of the present invention.

The table control element 4 moves the subject M to the imaging location by shifting the table 1 horizontally; implements lifting, rotation, and horizontal shifting to set the subject M in the desirable position; takes an image of the subject M; and retreats horizontally the subject M from the imaging location following the imaging. Such controls are implemented by controlling the table driving mechanism (not shown in FIG.) having a motor and an encoder (not shown in FIG.)

The FPD control element 5 control shifting of the FPD 3 in parallel to and along the body axis z which is the longitudinal direction of the subject M. Such controls are implemented by controlling the FPD driving mechanism (not shown in FIG.) having a rack, a pinion, the motor and the encoder (not shown in FIG.).

The high-voltage generation element 6 provides the X-ray tube 2 with the generated tube voltage and the tube electric current to irradiate the X-ray. The X-ray tube control element 7 controls the X-ray tube 2 subject to parallel-shifting in the opposite direction against the parallel-shifting of the FPD 3. Such controls are implemented by controlling the X-ray tube driving element (not shown in FIG.) having a pole, a screw, the motor and the encoder (not shown in FIG.).

In addition, the X-ray tube control element 7 controls setting a visual field of a collimator (not shown in FIG.) of the X-ray tube 2 side. According to the aspect of the present Embodiment, the collimator controlled to irradiate the fan-shaped X-ray beam having an expansion in the body axis z sets up the visual field.

The image processing element 9 and the controller 10 comprises a central processing unit (CPU) and so forth, and the memory element 11 comprises memory media typically including a ROM (read-only memory), a RAM (random-access memory) and so forth. In addition, the input element 12 comprises a pointing device represented by a mouse, a keyboard, a joy stick, a trackball and a touch panel and so forth.

Further, the CPU of the image processing element 9 implements the image processing corresponding to the programs, which execute a variety of image processings and are written and stored in the memory medium typically such as ROM, by reading out such programs from such memory medium. Particularly, according to the aspect of the present Embodiment, the CPU implements setting of the weighting factor and the weight addition to generate a reconstructed image.

The memory element 11 writes and stores the respective images processed by the image processing element 9. Other than the above, the memory element 11 writes and stores the threshold value set forth later, and the weighting factor set by the weighting factor setting element 9a of the image processing element 9 (referring to FIG. 2). The FPD control element 5 and the X-ray tube control element 7 comprise CPU and so forth as well as the image processing element 9 and the controller 10.

According to the aspect of the present Embodiment, the radiograph generation method is applied to the tomosynthesis that performs a tomographic imaging by reconstructing the projection images acquired by shifting the X-ray tube 2 and the FPD 3 respectively in the direction indicated in FIG. 1.

Referring to FIG. 2, the image processing element 9 comprises the weighting factor setting element 9a and the weight addition element 9b. The weighting factor setting element 9a corresponds to the weighting factor setting means of the present invention and the weight addition element 9b corresponds to the weight addition means of the present invention.

The weighting factor setting element 9a sets up a weight addition weighting factor combining each image processing algorithm based on the results of the respective pixel valued acquired by a plurality of different image processing algorithms each other. The inventor sets forth the detail of a specific function of the weighting factor setting element 9a according to FIG. 3 and later.

The weight addition element 9b performs a weight addition based on the set-up weighting factor. Then, such weight addition provides a radiograph (reconstructed image according to the aspect of the present Embodiment). The inventor, in addition, sets forth the detail of a specific function of the weight addition element 9b according to FIG. 3 and later.

Figure 3:
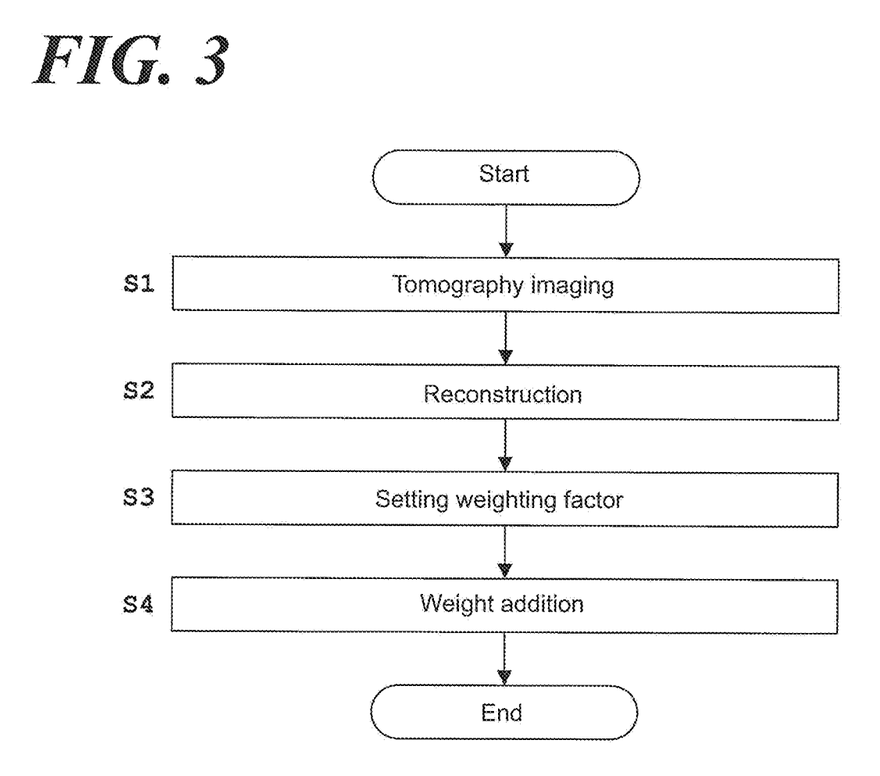
FIG. 3 is a flow chart illustrating the flow of a series of the radiograph generation method according to the aspect of the Embodiment.
Figure 4:
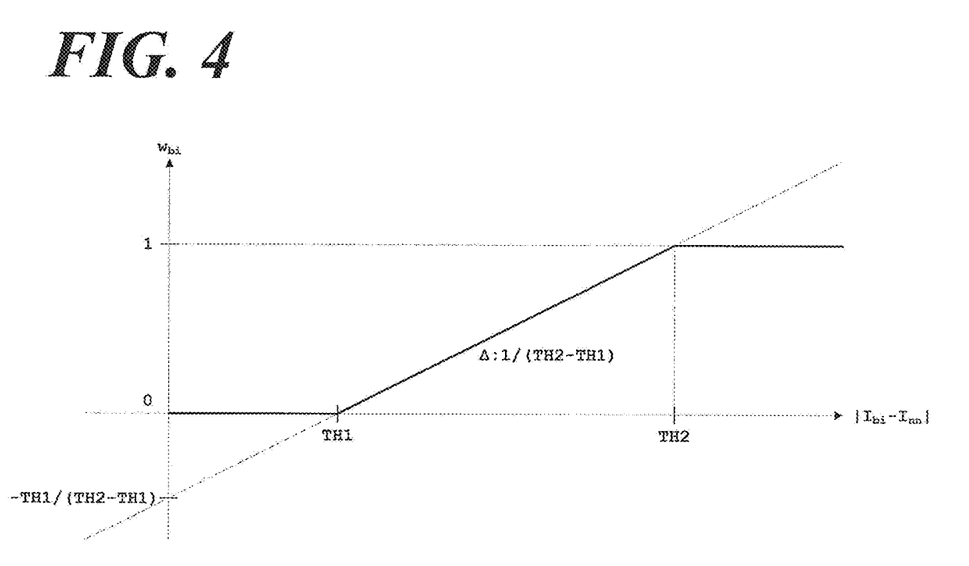
FIG. 4 is a graph in which the lateral axis is the absolute value relative to a backprojection pixel value and the ordinate axis is the weighting factor for the bilinear interpolation.

The inventor sets forth the specific radiograph generation method according to the aspect of the present Embodiment referring to FIG. 1 set forth above and in addition, FIG. 3 and FIG. 4. FIG. 3 is a flow chart illustrating the flow of a series of the radiograph generation method according to the aspect of the Embodiment. FIG. 4 is a graph in which the lateral axis is the absolute value relative to a backprojection pixel value and the ordinate axis is the weighting factor for the bilinear interpolation. The CPU of the image processing element 9 executes the program relative to the radiograph generation method referring to FIG. 3.

(Step S1) Tomographic Imaging

Referring to FIG. 1, the X-ray tube 2 irradiates an X-ray while shifting the X-ray tube 2 and the FPD 3 in the opposite direction to each other and the FPD 3 detects the X-ray irradiated to the subject from the different direction (projection angle) each other. The FPD 3 detects the X-rays, so that a plurality of X-ray images due to the irradiated X-rays respectively from the different direction each other to the subject M. The X-ray image is a projection data projected to the detection surface of the FPD 3.

(Step S2) Reconstruction

The filtered backprojection method, for which the nearest neighbor interpolation is the interpolation method, implements a (an image) reconstruction based on the X-ray images (projection images) acquired at the step S1. In parallel, the filtered backprojection method, for which the bilinear interpolation is the interpolation method, implements an image reconstruction based on the X-ray images (projection images) acquired at the step S1. The inventor skips setting forth the filtered backprojection using the nearest neighbor interpolation/bilinear interpolation as the interpolation method because of the known methods per se. The backprojection pixel values relative to the nearest neighbor interpolation is $I_{nn}$ and the backprojection pixel values relative to the bilinear interpolation is $I_{bi}$.

(Step 3) Setting a Weighting Factor

The weighting factor setting element 9a (referring to FIG. 2) sets up a weight addition weighting factor combining each image processing algorithm based on the results of the respective pixel valued acquired by a plurality of discrete image processing algorithms; and According to the aspect of the present Embodiment, an image processing algorithm applies the nearest neighbor interpolation algorithm and the bilinear interpolation algorithm. Therefore, according to the aspect of the present Embodiment, the weighting factor setting element 9a sets up the weighting factor based on the results of the respective pixel values acquired using the nearest neighbor interpolation and the bilinear interpolation.

Further specifically, the weighting factor is set up based on the absolute value $|I_{bi}-I_{nn}|$ of the difference between the backprojection pixel value $I_{nn}$ acquired by the nearest neighbor interpolation and the backprojection pixel value $I_{bi}$ acquired by the bilinear interpolation at the step S2. When the weighting factor corresponding to the nearest neighbor interpolation is a non-negative value less than 1, the weighting factor for the nearest neighbor interpolation is $w_{nn}$ and the weighting factor for the bilinear interpolation is $w_{bi}$, discrete weighting factors are set up so as to satisfy $w_{nn}+w_{bi}=1$. Hereinafter, the inventor unifies the sign of the weighting as $(1-w_{bi})$ denotes the weighting factor $w_{nn}$ for the nearest neighbor interpolation and the weighting factor $w_{bi}$ is the factor for the bilinear interpolation. In addition, if the weighting factor (i.e., bilinear ratio on mixing) is $w_{bi}[0, 1]$, the bilinear ratio is determined using the following formulas (1)-(3) based on the difference between the backprojection pixel values $I_{nn}$, $I_{bi}$.

$$w_{bi}=0, TH1>|I_{bi}-I_{nn}| \text{ is given.} \quad (1)$$

$$w_{bi}=(|I_{bi}-I_{nn}|-TH1)/(TH2-TH1), TH1<|I_{bi}-I_{nn}|<TH2 \text{ is given.} \quad (2)$$

$$w_{bi}=1, TH2<|I_{bi}-I_{nn}| \text{ is given.} \quad (3)$$

Here, TH1, TH2 are threshold values and satisfy the relational expression TH1<TH2. In addition, [a, b] denotes a closed segment and satisfying $\{x|a\le x\le b\}$. Accordingly, $w_{bi}$ [0, 1] denotes satisfying $\{w_{bi}|0\le w_{bi}\le 1\}$ (i.e., non-negative value smaller than 1).

Referring to FIG. 4, when the absolute value $|I_{bi}-I_{nn}|$ of the difference relative to the backprojection pixel value is lateral and the weighting factor $w_{bi}$ for the bilinear interpolation is ordinal, the function of the weighting factor $w_{bi}$, in which the absolute value $|I_{bi}-I_{nn}|$ of the difference is a variable, is a nondecreasing function (monotonically increasing function). Accordingly, it is set as the weighting factor $w_{bi}$ for the bilinear interpolation increases in accordance with increase of the absolute value $|I_{bi}-I_{nn}|$ of the difference and the weighting factor $w_{nn}$ for the nearest neighbor interpolation increases in accordance with decrease of the absolute value $|I_{bi}-I_{nn}|$ of the difference. As set forth above, it is given $w_{nn}+w_{bi}=1$, and the weighting factor $w_{bi}$ for the bilinear interpolation is given as $w_{bi}=1-w_{nn}$, so the fact in which the weighting factor $w_{nn}$ for the nearest neighbor interpolation increases in accordance with decrease of the absolute value $|I_{bi}-I_{nn}|$ of the difference denotes the fact in which the weighting factor $w_{bi}$ for the bilinear interpolation decreases in accordance with decrease of the absolute value $|I_{bi}-I_{nn}|$ of the difference.

Referring to FIG. 4, the above formulas (1)-(3), when the absolute value $|I_{bi}-I_{nn}|$ of the difference is in the range of threshold value smaller than 1 (TH1>$|I_{bi}-I_{nn}|$), the weighting factor $w_{bi}$ for the bilinear interpolation is a constant as $w_{bi}=0$, but in the range of which the absolute value $|I_{bi}-I_{nn}|$ of the difference is larger than the threshold value TH1 and smaller than the threshold value TH2 (TH1<$|I_{bi}-I_{nn}|$<TH2), the weighting factor $w_{bi}$ for the bilinear interpolation increases as the linear function having the gradient Δ as 1/(TH2−TH1) and the intercept −TH1/(TH2−TH1), and in the range of which the absolute value $|I_{bi}-I_{nn}|$ of the difference is bigger than the threshold value TH2 (TH2<$|I_{bi}-I_{nn}|$), the weighting factor $w_{bi}$ for the bilinear interpolation is a constant as $w_{bi}=1$. In addition, the graph referring to FIG. 4 is a continuous function, so when the absolute value $|I_{bi}-I_{nn}|$ of the difference is equal to the threshold value TH1 (TH1=$|I_{bi}-I_{nn}|$), either above formula (1) or (2) can be applied, and when the absolute value $|I_{bi}-I_{nn}|$ of the difference is equal to the threshold value TH2 (TH2=$|I_{bi}-I_{nn}|$), either above formula (2) or (3) can be applied.

The memory element 11 (referring to FIG. 1) writes and stores the weighting factors $w_{bi}$, $w_{nn}$ set by the weighting factor setting element 9a. Such step S3 corresponds to the step of setting the weighting factor.

(Step S4) Weight Addition

The weight addition element 9b (referring to FIG. 2) implements a weight addition using the following formula (4) based on the weighting factor $w_{bi}$, $w_{nn}$ (=$1-w_{bi}$) set at the step S3. The backprojection pixel value after weighting (mixing) is $I_{new}$.

$$I_{new}=w_{bi} \cdot I_{bi}+(1-w_{bi}) \cdot I_{nn} \quad (4)$$

Relative to the above formula (4), the region at which the absolute value of the difference between backprojection pixel values respectively acquired by the nearest neighbor interpolation and the bilinear interpolation is deemed as the edge with high-intensity difference, and then the weighting factor for the bilinear interpolation is set to be large (i.e., strengthen the weight), so the unevenness at such edge region can be reduced. Reversely, the nearest neighbor interpolation sets up the weighting factor $w_{nn}$ to be large in the region at which the absolute value $|I_{bi}-I_{nn}|$ of the difference set forth above is small (i.e., strengthen the weight), so that the grid artifact due to the non-conformity of S/N can be reduced. Such step S4 corresponds to the step of weight addition of the present invention.

In such way, a radiograph (reconstructed image here) can be acquired by arranging the backprojection pixel value $I_{new}$ every pixel following the weighting obtained by the above formula (4). The radiograph (reconstructed image) is written and stored in the memory element 11.

In such way, the feature of the present invention is that the weighting factor is set up based on the results of the respective pixel valued acquired by a plurality of discrete image processing algorithms (the nearest neighbor interpolation and the bilinear interpolation); and a weight addition combining discrete image processing algorithms is implemented based on such set-up weighting factor. It is noted; that Patent Document 2. JP 4,293,307 (JP 2005/522304) discloses a bilinear interpolation and a nearest neighbor interpolation as an interpolation method for image reconstruction, but a weight addition is not being taught at all.

The radiograph generation method according to the aspect of the present Embodiment performs weight addition combining each image processing algorithm to combine a plurality of discrete image processing algorithms (the nearest neighbor interpolation and the bilinear interpolation according to the aspect of the Embodiment 1) each other. For such purpose, the weighting factor of the weight addition is set up based on the results of the pixel values acquired by the respective image processing algorithms (according to the aspect of the present Embodiment, the absolute value $|I_{bi}-I_{nn}|$ of the difference between the backprojection pixel value $I_{nn}$ acquired by the nearest neighbor interpolation and the backprojection pixel value $I_{bi}$ acquired by the bilinear interpolation). A radiograph (reconstructed image according to the aspect of the present Embodiment), in which noises and artifacts are reduced by setting the weighting factor of the image processing algorithm causing a negative effect on the region of some pixel values to be minimal and setting the weighting factor of the (other) image processing algorithm causing a positive effect on the same pixel value region to be maximum based on the results of the pixel values acquired by the respective image processing algorithms (absolute value $|I_{bi}-I_{nn}|$ of the difference), can be acquired.

According to the aspect of the present Embodiment, one example of the radiograph is a reconstructed image. According to the aspect of the present Embodiment, the radiograph generation method sets the weighting factor based on the results of the respective backprojection pixel values acquired by a plurality of the discrete image processing algorithms (absolute value $|I_{bi}-I_{nn}|$ of the difference according to the aspect of the present Embodiment).

According to the aspect of the present Embodiment, the weighting factors corresponding to every image processing algorithm are set cooperatively. Specifically, the weighting factor corresponding to every image processing algorithm is a non-negative value less than 1 and n is an integer bigger than 2; and given each weighting factor is $w_1, w_2, \ldots, w_n$, (according to the aspect of the present Embodiment, n=2 and each weighting factor $w_1$, $w_2$ corresponds to $w_{nn}$, $w_{bi}$), each weighting factor is set as satisfying $w_1+w_2+\ldots+w_n=1$ (according to the aspect of the present Embodiment, satisfying $w_{nn}+w_{bi}=1$). In such way, the discrete weighting factor satisfying $w_1+w_2+\ldots+w_n=1$ is set up, so that the discrete weighting factors can be set up cooperatively. Accordingly, when it is desirable that the effect of a certain image processing algorithm is strong, the weighting factor relative to such image processing algorithm is set to be large, so that the weighting factor relative to the rest of image processing algorithms can be set to be minimal. Reversely, when it is desirable that the effect of a certain image processing algorithm is weak, the weighting factor relative to such image processing algorithm is set to be minimal, so that the weighting factor relative to the rest of image processing algorithms can be set to be large.

According to the aspect of the present Embodiment, the image processing algorithm is the nearest neighbor interpolation and the bilinear interpolation; in which it is preferable that the image processing algorithm sets up the weighting factor $w_{nn}$, $w_{bi}$ based on the result of the respective pixel values obtained by the nearest neighbor interpolation and the bilinear interpolation (absolute value $|I_{bi}-I_{nn}|$ of the difference according to the aspect of the present Embodiment) relative to the weighting factor set-up step (step S3), and implements the weight addition in regard to the nearest neighbor interpolation and the bilinear interpolation relative to the weight addition step (step S4). The bilinear interpolation sets up the weighting factor $w_{bi}$ in the region (region having the edge with high-intensity difference) so as to be large, at which the negative effect due to the nearest neighbor interpolation is strong, so that the bilinear interpolation can reduce the uneven artifact. Reversely, the nearest neighbor interpolation sets up the weighting factor $w_{nn}$ in the region (region having the non-conformity of S/N) so as to be large, at which the negative effect due to the bilinear interpolation is strong, so that the nearest neighbor interpolation can reduce the grid artifact due to the non-conformity of S/N. In such way, the nearest neighbor interpolation and the bilinear interpolation can reduce not only the calculation cost, the loading, the calculation-time, but also the uneven artifact and the grid artifact due to the non-conformity of S/N, despite such easy and convenient interpolation algorithm.

According to the aspect of the present Embodiment, when the image processing algorithms are the nearest neighbor interpolation and the bilinear interpolation, such image processing algorithm is useful for the following invention. Specifically, it is useful when the radiograph is a reconstructed image, an X-ray is applied, and the weighting factor is set up based on the results of the backprojection pixel values $I_{nn}$ acquired by the nearest neighbor interpolation and the backprojection pixel values $I_{bi}$ acquired by the bilinear interpolation (absolute value $|I_{bi}-I_{nn}|$ of the difference according to the aspect of the present Embodiment). In such way, when the radiation is an X-ray, the above uneven artifact and the grid artifact due to non-conformity of S/N easily take place; but when the weighting factor is set up based on the results of the backprojection pixel values $I_{nn}$ acquired by the nearest neighbor interpolation and the backprojection pixel values $I_{bi}$ acquired by the bilinear interpolation (absolute value $|I_{bi}-I_{nn}|$ of the difference according to the aspect of the present Embodiment), the uneven artifact and the grid artifact due to non-conformity of S/N can be reduced.

According to the aspect of the present Embodiment, even if the image processing algorithms are the nearest neighbor interpolation and the bilinear interpolation, the radiograph is the reconstructed image and the radiation is the X-ray; the following setting is preferable. Specifically, it is preferable that based on the absolute value $|I_{bi}-I_{nn}|$ of the difference between the backprojection pixel values $I_{nn}$ acquired by the nearest neighbor interpolation and the backprojection pixel values $I_{bi}$ acquired by the bilinear interpolation, the weighting factor $w_{bi}$ for the bilinear interpolation is being set to be large in accordance with increasing of the absolute value $|I_{bi}-I_{nn}|$ of the difference and the weighting factor $w_{nn}$ for the nearest neighbor interpolation method is being set up to be large in accordance with decreasing of the absolute value $|I_{bi}-I_{nn}|$ of the difference. The region at which the absolute value $|I_{bi}-I_{nn}|$ of the difference set forth above is deemed as the edge with high-intensity difference, and then the weighting factor $w_{bi}$ for the bilinear interpolation is set to be large (i.e., strengthen the weight), so that the unevenness at such edge region can be reduced. Reversely, the nearest neighbor interpolation sets up the weighting factor $w_{nn}$ to be large in the region at which the absolute value $|I_{bi}-I_{nn}|$ of the difference set forth above is small (i.e., strengthen the weight), so that the grid artifact due to the non-conformity of S/N can be reduced.

Further specifically, it is preferable that the following respective weighting factors are set up cooperatively. Specifically, as repeatedly set forth, when the weighting factor corresponding to the nearest neighbor interpolation is a non-negative value not more than 1, the weighting factor for the nearest neighbor interpolation is $w_{nn}$ and the weighting factor for the bilinear interpolation is $w_{bi}$, it is preferable that each weighting factor is set up so as to satisfy $w_{nn}+w_{bi}=1$. The region at which the absolute value $|I_{bi}-I_{nn}|$ of the difference set forth above is deemed as the edge with high-intensity difference, and then the weighting factor $w_{nn}$ for the nearest neighbor interpolation is set up to be minimal to reduce unevenness at such edge region, so that the rest of the weighting factors $w_{bi}$ for the bilinear interpolation can be set to be large (i.e., strengthen the weight). Consequently, the unevenness in the edge region decreases. Reversely, relative to the region at which the absolute value $|I_{bi}-I_{nn}|$ of the difference set forth above is small, the weighting factors $w_{bi}$ for the bilinear interpolation is set up to be minimal, the rest of the weighting factor $w_{nn}$ for the nearest neighbor interpolation can be set up to be large (i.e., strengthen the weight). Consequently, the grid artifact due to the non-conformity of S/N decreases.

In addition, relative to the image processing apparatus (image processing element 9) according to the aspect of the present Embodiment, the radiograph (reconstructed image according to the aspect of the present Embodiment), in which noises and artifacts are reduced by setting the weighting factor of the image processing algorithm causing a negative effect on the region of some pixel values to be minimal and setting the weighting factor of the (other) image processing algorithm causing a positive effect on the same pixel value region to be maximum based on the results of the pixel values acquired by the respective image processing algorithms (absolute value $|I_{bi}-I_{nn}|$ of the difference), can be acquired, corresponding to the result of the pixel values (the absolute value $|I_{bi}-I_{nn}|$ of the difference between the backprojection pixel value $I_{nn}$ acquired by the nearest neighbor interpolation and the backprojection pixel value $I_{bi}$ acquired by the bilinear interpolation) by the respective algorithms (the nearest neighbor interpolation and the bilinear interpolation according to the aspect of the present Embodiment).

Experimental Results

Figure 7:
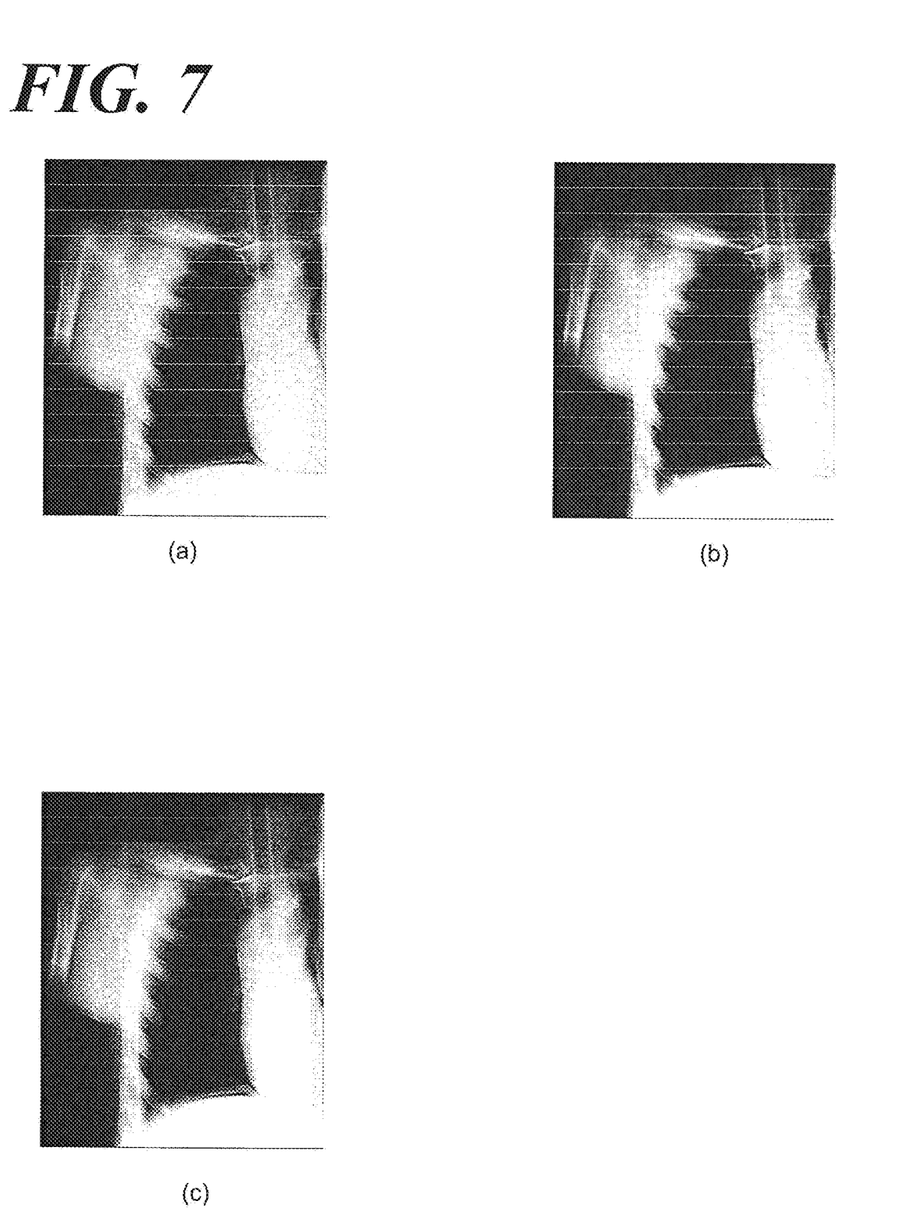
FIG. 7 is illustrating an experimental result relative to the shoulder of the human subject.
Figure 8:
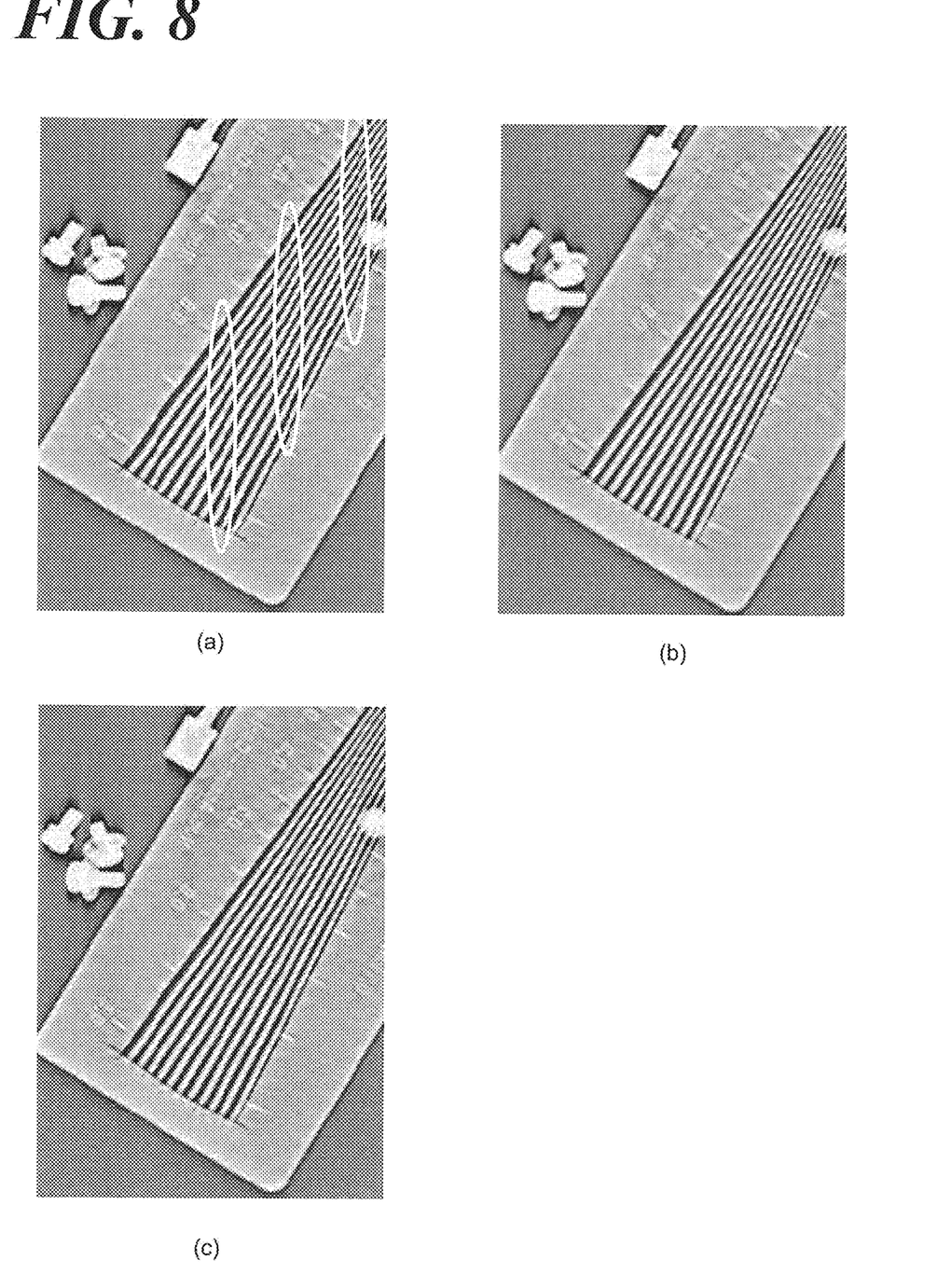
FIG. 8 is illustrating an experimental result relative to the subject other than human.

Referring to FIG. 7, FIG. 8, the inventor sets forth the results using the method of the present invention (the weight addition of the nearest neighbor interpolation and the bilinear interpolation). In addition, for the comparison purpose of the method of the present invention, the nearest neighbor interpolation and the bilinear interpolation are also illustrated in FIG. FIG. 7(a)-FIG. 7(c) are the experimental result of the shoulder of a human subject. FIG. 7(a) is the image acquired using the nearest neighbor interpolation. FIG. 7(b) is the image acquired using the bilinear interpolation. FIG. 7(c) is the image acquired using the method of the present invention. FIG. 8(a)-FIG. 8(c) are the experimental result of other than the human subject. FIG. 8(a) is the image acquired using the nearest neighbor interpolation. FIG. 8(b) is the image acquired using the bilinear interpolation. FIG. 8(c) is the image acquired using the method of the present invention.

Referring to FIG. 7(b), it is confirmed that grid artifacts due to the non-conformity of S/N appears when the bilinear interpolation is applied. In contrast, referring to FIG. 7(c), it is confirmed that no grid artifacts due to the non-conformity of S/N appears when the bilinear interpolation according to the present invention is applied and the non-conformity of S/N is removed (improved).

Referring to FIG. 8(a), relative to the circled area with the white line, it is confirmed that uneven artifacts appear near the edge when the nearest neighbor interpolation is applied. In contrast, referring to FIG. 8(c), it is confirmed that no uneven artifact appears when the method according to the present invention is applied and the method according to the present invention keeps the natural appearance of the image near the edge.

The present invention is not limited to the aspect of the Embodiment set forth above and further another alternative Embodiment can be implemented set forth below.

(1) According to the aspect of the Embodiment set forth above, the radiation is X-ray, but other radiation than X-ray (e.g., α-ray, β-ray, γ-ray and so forth) can be applied.

(2) According to the aspect of the Embodiment as set forth above, the radiograph is an reconstructed image, but the image processing is not limited to the backprojection relative to such reconstruction. The aspect of the present intension can be applied to an image processing on rotation, expansion, reduction and so forth.

(3) According to the aspect of the Embodiment as set forth above, the subject is a human, but the subject can be such as a substrate subject to the non-destructive inspection and so forth.

(4) According to the aspect of the Embodiment as set forth above, an imaging is represented by the tomographic imaging, but the present invention can be applied to an fluoroscopy monitoring a radiograph in real-time by irradiating a weaker radiation dosage than the imaging.

(5) According to the aspect of the Embodiment as set forth above, an image processing apparatus (image processing element 9 of the Embodiment) is incorporated in the fluoroscopic apparatus such as a tomographic imaging apparatus, but the image processing apparatus can be stand-alone.

(6) According to the aspect of the Embodiment set forth above, the radiograph generation method is applied to the tomosynthesis referring to FIG. 1, but the applicable tomographic imaging operational method is not particularly limited thereto. For example, the present invention can be applied to an X-ray CT (computed tomography) apparatus that implements the tomographic imaging revolving around the central axis of body axis of the subject; or the tomographic imaging rotating along with the C-arm, in which one end of C-arm forming a curve holds the X-ray tube and the other end thereof holds the X-ray detector. In addition, the radiation can be other than X-ray as set forth above.

(7) According to the aspect of the present Embodiment set forth above, the image processing algorithms are the nearest neighbor interpolation and the bilinear interpolation; and the weight addition combing discrete image processing algorithms to combine the two image processing algorithms comprising the nearest neighbor interpolation and the bilinear interpolation is implemented, but the number of the image processing algorithm is not particularly limited as far as the number is plural. For example, the spline interpolation method in addition to the nearest neighbor interpolation and the bilinear interpolation can be combined and the number of the image processing algorithm can be higher than 3.

(8) According to the aspect of the Embodiment set forth above, the weighting factors corresponding to every image processing algorithm are set cooperatively and respectively, but the weighting factor can be set up discretely and independently. For example, one weighting factor can be set to be variable independently from the other weighting factor while fixing the one weighting factor, and reversely, while the other weighting factor can be set to be variable, the rest of the weighting factors can be fixed independently from the other.

(9) According to the aspect of the Embodiment set forth above, the image processing algorithms are the nearest neighbor interpolation and the bilinear interpolation, but such image processing algorithm is not limited to the nearest neighbor interpolation and the bilinear interpolation. The Lanczos interpolation and the spline interpolation can be applied. Considering that even simple interpolation algorithm can, however, reduce noises and artifacts, an easy and convenient interpolation algorithm, such as the nearest neighbor interpolation, the bilinear interpolation or the spline interpolation method, is more advantageous than a precious interpolation algorithm such as the Lanczos interpolation. Reducing not only the calculation cost, the loading, the calculation-time, but also noises and artifacts can be achieved by applying such easy and convenient algorithm.

(10) According to the aspect of the Embodiment set forth above, the weighting factor is automatically set up by the weighting setting means (weighting factor setting element 9a according to the Embodiment) comprising a CPU and so forth, but the automatic setting of the weighting factor is not mandatory. Instead, a pointing device such as the input element 12 comprises the weighting factor setting means and the operator can manually set up the weighting factor based on the results displayed on the monitor, which displays the results of the respective pixel values acquired by the respective image processing algorithms.

(11) According to the aspect of the Embodiment set forth above, the results of the pixel values acquired by the respective image processing algorithms is the difference between pixel values (according to the aspect of the present Embodiment, the absolute value $|I_{bi}-I_{nn}|$ of the difference between the backprojection pixel value $I_{nn}$ acquired by the nearest neighbor interpolation and the backprojection pixel value $I_{bi}$ acquired by the bilinear interpolation), but not limited to the difference between the pixel values. While acquiring the ratio of the pixel values, the weighting factor can be set up based on the ratio of such pixel values.

(12) According to the aspect of the Embodiment set forth above, the weighting factor, e.g., referring to FIG. 4, is constant in the range of threshold value less than TH1 and in the range of threshold value more than TH2, and increases continuously in the open-range between threshold values TH1 and TH2, but the weighting factor is not limited to the aspect referring to FIG. 4. Regardless of the threshold value, the weighting factor can be set up by continuously increasing or decreasing, or the weighting factor can be set up by increasing or decreasing using a trigonometrical function or a polynomial equation more than quadratic function. In addition, the weighting factor is required to be a continuous function and the weighting factor can be increased or decreased stepwise.

REFERENCE OF SIGNS

9 Image processing element
9a Weighting factor setting element
9b weight addition element
$I_{nn}$ Backprojection pixel value acquired by the nearest neighbor algorithm
$I_{bi}$ Backprojection pixel value acquired by the bilinear interpolation
$w_{nn}$ Weighting factor in the nearest neighbor algorithm
$w_{bi}$ Weighting factor in the bilinear interpolation
TH1, TH2 Threshold value
$I_{new}$ Back-projection pixel value after weighting

What is claimed is:

1. A reconstructed image generation method, that generates a reconstructed image, comprising steps of:
   obtaining a projection image;
   determining a pixel value and a pixel location to reconstruct said reconstructed image using discrete image processing algorithms based on a plurality of pixel image location and pixel image value of the obtained projection image;
   carrying out respectively a backprojection relative to said discrete image processing algorithms;
   setting a weighting factor of a weight addition based on a result of a difference of pixel values of a corresponding pixel relative to volume data following backprojection of image processing algorithms; and
   adding a weight addition relative to pixel values at said corresponding pixel based on a set-up weighting factor; and
   wherein said reconstructed image is acquired by said weight addition;
   wherein said image processing algorithms are both a nearest neighbor interpolation and a bilinear interpolation, said step of setting said weighting factor sets up said weighting factor based on a result of respective pixel values acquired by using both said nearest neighbor interpolation and said bilinear interpolation, said weight addition step implements an weight addition relative to both said nearest neighbor interpolation and said bilinear interpolation;
   wherein said radiation is an X-ray;
   said step of setting said weighting factor sets up said weighting factor based on a result of a backprojection pixel value acquired by both said nearest neighbor interpolation and a backprojection pixel value acquired by said bilinear interpolation;
   said step of setting said weighting factor sets up said weighing factor based on an absolute value of a difference between a backprojection pixel value acquired by said nearest neighbor interpolation and a backprojection pixel value acquired by said bilinear interpolation;
   a weighting factor for said bilinear interpolation is set up to be larger in accordance with an increasing of said absolute value of the difference and a weighting factor for said nearest neighbor interpolation is set up to be larger in accordance with a decreasing of said absolute value of the difference;
   wherein given said weighting factor corresponding to said nearest neighbor interpolation and said bilinear interpolation is a non-negative value not more than 1, then a weighting factor $w_{nn}$ for said nearest neighbor interpolation and a weighting factor $w_{bi}$ for said bilinear interpolation, are said discrete weighting factors and satisfy $w_{nn}+w_{bi}=1$;
   wherein said backprojection pixel value after weighing is equal to the sum of the product of a weighting factor $w_{bi}$ and a backprojection pixel value acquired by the bilinear interpolation and the product of the difference of 1 minus the weighting factor $w_{bi}$ and a backprojection pixel value acquired by the nearest neighbor interpolation; and
   wherein said reconstructed image is acquired by arranging each of said backprojection pixel value after weighting.

2. The reconstructed image generation method, according to claim 1, wherein:
   given that said weighting factor corresponding to every said image processing algorithm is a non-negative value not more than 1, n is an integer not smaller than 2, and discrete weighting factors are $w_1, w_2, \ldots, w_n$; then said discrete weighting factors satisfy $w_1+w_2+\ldots+w_n=1$.

3. A reconstructed image generation apparatus, that generates a reconstructed image, comprising:
   a projection image processor configured to obtain a projection image;
   a determining circuit configured to determine a pixel value and a pixel location to reconstruct said reconstructed image using discrete image processing algorithms based on a plurality of pixel image location and pixel image value of the obtained projection image;
   a backprojection processor that carries out respectively a backprojection relative to said discrete image processing algorithms;
   a weighting factor setting circuit configured to set-up a weighting factor of a weight addition based on a result of a difference of pixel values of a corresponding pixel relative to volume data following backprojection of image processing algorithms;
   a weight addition circuit configured to implement said weight addition relative to pixel values at said corresponding pixel based on a set-up weighting factor; and
   wherein said reconstructed image is acquired by determining and arranging a new backprojection pixel value for each pixel that is determined after weighting as being equal to the sum of the product of a weighting factor for the bilinear interpolation and a packprojection pixel value acquired by the bilinear interpolation and the product of the difference of 1 minus the weighting factor for the bilinear interpolation and a backprojection pixel value acquired by the nearest neighbor interpolation.

* * * * *